United States Patent [19]

Ahnell et al.

[11] 4,182,656
[45] * Jan. 8, 1980

[54] METHOD FOR DETECTING THE PRESENCE OF BIOLOGICALLY ACTIVE AGENTS UTILIZING $^{13}$C-LABELED SUBSTRATES

[75] Inventors: Joseph E. Ahnell, Baltimore; Rodney L. Broman, Falston; John R. Waters, Towson, all of Md.

[73] Assignee: Johnston Laboratories, Inc., Cockeysville, Md.

[*] Notice: The portion of the term of this patent subsequent to Feb. 14, 1995, has been disclaimed.

[21] Appl. No.: 722,270

[22] Filed: Sep. 10, 1976

[51] Int. Cl.$^2$ .................. C12K 1/04; G01N 27/78; G01N 33/16
[52] U.S. Cl. .................................................. 435/34
[58] Field of Search ............... 195/103.7, 103.5 R, 195/103.5 M, 127; 23/230 B, 230.3, 230.6; 424/1; 250/303

[56] References Cited

U.S. PATENT DOCUMENTS

| | | | |
|---|---|---|---|
| 2,914,447 | 11/1959 | Levin | 23/230.3 |
| 3,676,679 | 7/1972 | Waters | 195/127 |
| 3,788,814 | 1/1974 | Goldblatt et al. | 23/230.6 |
| 3,844,894 | 10/1974 | Kronick et al. | 195/127 |
| 3,935,073 | 1/1976 | Waters | 195/103.7 |
| 3,969,496 | 7/1976 | Schrot | 23/230 B |
| 4,073,691 | 2/1978 | Ahnell et al. | 195/103.5 M |

OTHER PUBLICATIONS

Matschke et al., "Carbon-13/Carbon-12 Study of the Developing Biogas During Microbial Decomposition of Humic Acids and Bitumen", Chem. Abstracts, vol. 77, No. 13, p. 195 (1972), No. 85410w.
Gregg et al., "Search for Biological Effects of Carbon-13 Enrichment in Developing Mammalian Systems," Chem. Abstracts, vol. 84, No. 19, p. 200 (1976), No. 132073v.
Close et al., "Detection of the Stable Isotopes of Carbon Using a 3-MV Van de Graaff and the Application to Environmental and Biological Studies," Chem. Abstracts, vol. 81, No. 4, (1974) No. 19908w.
Waller et al., "Mass Spectrometry of Biosynthetically labeled Ricinine," Chem. Abstracts, vol. 65, (1966), No. 10947e.
Siri, Isotopic Tracers and Nuclear Radiations, 1st ed., McGraw-Hill Book Co., Inc., New York (1949) pp. 300, 301, 514, 515, 542.

Primary Examiner—Thomas G. Wiseman

[57] ABSTRACT

A sample of material to be tested for the presence of biologically active agents, such as bacteria, is introduced into a sealable container partially filled with a culture medium comprising a $^{13}$C-labeled fermentable substrate, the remainder of the container being filled with a culture gas, the container and its contents are subjected to conditions conducive to biological activity for a predetermined period sufficient for fermentation of the medium to produce carbon dioxide after which the ratio of $^{13}CO_2$ to $^{12}CO_2$ in the culture gas in the container is determined and compared to the initial ratio of $^{13}CO_2$ to $^{12}CO_2$ in the culture gas in order to detect any differences indicating the presence of biologically active agents in the sample.

14 Claims, 3 Drawing Figures

METHOD FOR DETECTING THE PRESENCE OF BIOLOGICALLY ACTIVE AGENTS UTILIZING $^{13}$C-LABELED SUBSTRATES

BACKGROUND OF THE INVENTION

In many fields of endeavor it is important to be able to determine whether or not substances are contaminated with biologically active agents such as bacteria and the like. Examples of such fields are the medical field, the food processing industry, the pharmaceutical industry, the cosmetics industry, the field of public health, and in interplanetary space vehicles.

In the past, it has been a standard practice to place a sample of a material to be tested for the presence of biologically active agents in an appropriate growth medium on a Petri dish and to make visual observations of the resulting microbial growth, if any. Not only are such culturing methods show and laborious, but because they depend on the subjective judgement of individual human observers, the result obtained is not uniformly reliable.

Techniques have also been developed for detection of bacteria which involve incubating a sample of material to be tested in a closed container with a radioactive isotope labeled culture medium and monitoring the atmosphere in the container above the medium to determine whether or not radioactive gases are produced. A system of this type is disclosed in U.S. Pat. Nos. 3,676,679 and 3,935,073. Such systems are rapid and reliable, but they suffer from a number of disadvantages. In the first place, radioactively labeled materials are not inexpensive and require special handling during storage, use and disposal. Moreover, although the levels of radioactivity encountered in using such systems are very low, prospective users may be deterred by personal fears of radioactivity. The use of radioactive isotopes in instrumental systems has generally been considered necessary in order to facilitate detection of minute quantities of metabolic product gases thereby to detect the presence of biologically active species. There exists a need for a practicable non-radioactive instrumental system for measuring metabolically produced gases in order to detect bacteria and the like.

Accordingly, it is an object of the present invention to provide a rapid method for detecting the presence or absence of biologically active agents.

Another object of the invention is to provide a method for detecting the presence or absence of biologically active agents which uses comparatively inexpensive materials.

It is a further object of the present invention to provide an instrumental method for detecting the presence or absence of biologically active agents which is not subject to the vagaries of subjective human observations.

Another object of the present invention is to provide an instrumental system for detecting the presence or absence of biologically active agents which avoids the use of radioactive materials.

Further objects of the invention will be apparent from a consideration of the following description.

SUMMARY OF THE INVENTION

These and other objects of the invention are achieved by providing a method for detecting the presence of biologically active agents comprising the steps of providing a sealed, sterile container partially filled with a sterile culture medium comprising a $^{13}$C-labeled substrate fermentable to produce $^{13}CO_2$; said container further containing a sample of material to be tested for biological activity; the remainder of said container being filled with a culture gas containing a known initial ratio of $^{13}CO_2$ to $^{12}CO_2$; subjecting the sealed container and its contents to conditions conducive to biological activity for a predetermined period of time sufficient for fermentation of the $^{13}$C-labeled substrate to produce $^{13}CO_2$; thereafter measuring the ratio of $^{13}CO_2$ to $^{12}CO_2$ in the culture gas, and comparing the measured ratio of $^{13}CO_2$ to $^{12}CO_2$ to the known initial ratio of $^{13}CO_2$ to $^{12}CO_2$.

In its most preferred embodiment the invention involves providing a sterile, sealable container partially filled with a sterile culture medium comprising a $^{13}$C-labeled substrate fermentable to produce $^{13}CO_2$, the remainder of said container being filled with a culture gas; said container comprising means for introducing a sample of material to be tested for the presence of biologically active agents into the container; introducing a sample of material to be tested for biological activity into said container and sealing said container; determining the initial ratio of $^{13}CO_2$ to $^{12}CO_2$ in said culture gas in said container; subjecting the sealed container and its contents to conditions conducive to biological activity for a predetermined period of time sufficient for fermentation of the $^{13}$C-labeled substrate to produce $^{13}CO_2$; thereafter withdrawing a sample of the culture gas from said container and determining the ratio of $^{13}CO_2$ to $^{12}CO_2$ in said culture gas sample, and comparing the ratio of $^{13}CO_2$ to $^{12}CO_2$ in the culture gas sample to the initial ratio of $^{13}CO_2$ to $^{12}CO_2$ in the culture gas.

A further preferred embodiment of the invention involves providing a pair of identical sterile, sealable containers partially filled with equal amounts of a sterile culture medium comprising a $^{13}$C-labeled substrate fermentable to produce $^{13}CO_2$, the remainder of each of said containers being filled with a culture gas; inoculating one of said containers by introducing a sample of material to be tested for biological activity into said one container and sealing both containers; subjecting both containers and their contents to conditions conducive to biological activity for a predetermined period of time sufficient for fermentation of the $^{13}$C-labeled substrate to produce $^{13}CO_2$; thereafter determining the ratio of $^{13}CO_2$ to $^{12}CO_2$ in each of said containers and comparing the ratio of $^{13}CO_2$ to $^{12}CO_2$ in the inoculated and uninoculated containers. Determination of the ratio of $^{13}CO_2$ to $^{12}CO_2$ may be effected by taking mass spectra of culture gas samples and comparing the relative sizes of the spectrum peaks corresponding to the molecular weights of $^{13}CO_2$ to $^{12}CO_2$ respectively for each spectrum. As used in this application the terms $^{13}CO_2$ and $^{12}CO_2$ refer to compounds incorporating the most abundant isotope of oxygen, namely that which has an atomic weight of 16, so that the resulting carbon dioxide molecules have molecular weights of 45 and 44, respectively.

DETAILED DESCRIPTION OF THE PREFERRED EMBODIMENTS

Figure 1:
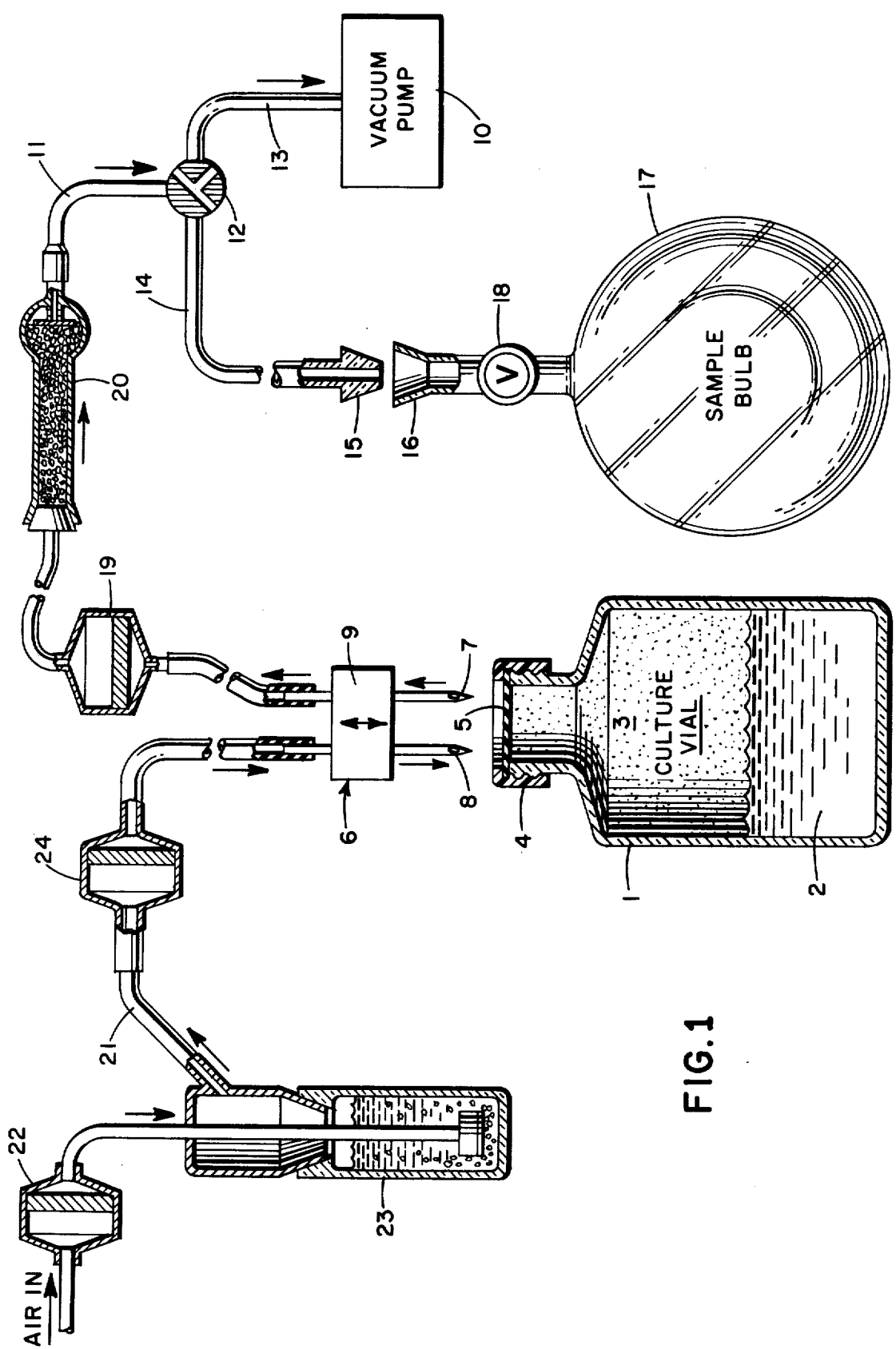
FIG. 1 is a schematic representation of apparatus utilized in practicing the method of the invention.

Turning now to FIG. 1, reference numeral 1 designates a culture vial utilized in the practice of the method of the present invention. Vial 1 is partially filled with a culture medium 2. Typical culture media generally contain water, a carbon source, a nitrogen source, calcium, magnesium, potassium, phosphate, sulfate, and trace amounts of other minor elements. The carbon source of the culture medium utilized in the method of the present invention comprises a $^{13}$C-labeled compound fermentable to produce $^{13}CO_2$. The carbon source may be carbohydrate, amino acid, mono- or dicarboxylic acid or salt thereof, polyhydroxy alcohol, hydroxy acid or other metabolizable carbon compound. Representative carbon compounds include carbohydrates such as glucose, sucrose, fructose, xylose, maltose, lactose, etc., amino acids such as lysine, glycine, alanine, tyrosine, threonine, histidine, leucine, etc. and mixtures thereof. Desirably, all of the carbon atoms in the fermentable carbon compounds in the culture medium are $^{13}$C-atoms. However, it will be appreciated that not all of the carbon atoms need be $^{13}$C-atoms so long as there are enough $^{13}$C-atoms at appropriate sites in the molecules to produce an appreciable amount of $^{13}CO_2$ upon fermentation of the substrate. In a similar vein, it is desirable to use a minimally supportive culture medium in addition to the labeled carbon source in order to constrain any biologically active agents present in a test inoculum to metabolize the isotopically labeled substrate. However, unlabeled carbon compounds may be present in the culture medium. The presence of substrate materials which ferment to produce $^{12}CO_2$ somewhat reduces the sensitivity of the method of the invention but does not destroy the efficacy of the test.

The nitrogen source may be nitrate, nitrite, ammonia, urea or any other assimilable organic or inorganic nitrogen source. An amino acid might serve as both a carbon and a nitrogen source. Sufficient nitrogen should be present to facilitate cell growth.

A variety of calcium, potassium and magnesium salts may be employed in the culture medium including chlorides, sulfates, phosphates and the like. Similarly, phosphate and sulfate ions can be supplied as a variety of salts. As such materials are conventional in fermentation media, the selection of specific materials as well as their proportions is thought to be within the skill of the art.

The so called minor elements which are present in trace amounts are commonly understood to include manganese, iron, zinc, cobalt and possibly others.

Due to the fact that most biologically active species cannot function in strongly acidic or strongly alkaline media, suitable buffers such as potassium or ammonium phosphates may be employed, if desired, to maintain the pH of the culture medium near neutral.

Examples of well known culture media which may be used in the present invention are peptone broth, tryptic soy broth, nutrient broth, thioglycolate broth, or brain-heart infusion broth.

As noted previously, culture medium 2 fills only a portion of vial 1. The remainder of the vial is filled with gas referred to herein as the culture gas. The culture gas may be any gas or mixture of gases which will support the growth of biologically active agents. Under most circumstances, ordinary air provides an acceptable culture gas for aerobic organisms. Cylinder gas may be utilized as the culture gas instead of ambient air. When anaerobic bacteria are of interest, the culture gas should be oxygen free. A nitrogen and carbon dioxide culture gas may be used for anaerobic organisms. Reference numeral 3 is utilized to designate the culture gas. Vial 1 with the medium and culture gas therein is sealed with a cap 4. In the illustrated embodiment, cap 4 comprises a self-sealing rubber septum which allows material to be injected into or removed from the vial through hollow needles. The sealed vials with culture medium and culture gas inside are sterilized in an autoclave to prevent disruption of tests by biologically active agents from sources other than the test material.

To initiate the testing of a material for the presence of biologically active agents, a sample of the material is introduced into a sterile vial containing culture medium and culture gas. If the sample is a fluid, such as blood or urine, introduction of the sample can be effected by injecting it through septum 5 with a hypodermic needle. Care should be taken to sterilize the needle and the septum before making the injection in order to prevent contamination of the test vial. Solid materials may be tested by utilizing vials provided with apertures through the vial walls closed by tightly sealing, removable and replaceable caps.

After inoculation with the test material, the inoculated vial is incubated, i.e., subjected to conditions conducive to biological activity for a predetermined period of time sufficient for fermentation of the $^{13}$C-labeled culture medium to produce $^{13}CO_2$. It should be noted that the terms "ferment" and "fermentation" are not used herein in any technically restrictive sense, but are intended to refer to biological activity generally, including without limitation the action of bacteria, yeasts, fungi, algae, protozoa, viruses and the like. If photoresponsive or phototoxic microorganisms are of interest, light should be provided or excluded accordingly.

Since most medically significant bacteria achieve their maximum growth rates at temperatures of approximately 36° C. plus or minus 1° C., the culture vials are desirably maintained at a temperature lying in the range from about 35° C. to about 37° C. It is understood, however, that not all biologically active agents exhibit maximum growth within the recited temperature range. If it is of particular interest to determine whether or not a specific microorganism which grows better at some other temperature is present, then the temperature should be maintained at approximately that temperature at which the organism in question exhibits maximum growth.

Agitation of the culture medium is useful both to promote growth of biologically active agents which may be present and also to liberate carbon dioxide, produced by the metabolic activity of biologically active agents, from the culture medium into the culture gas. A conventional shaking table may be utilized to effect gentle agitation. Alternatively, the culture medium can be stirred with a magnetic stirring bar magnetically coupled to a rotating magnet disposed beneath the culture vial.

The length of the incubation period before the culture gas is analyzed and/or between subsequent tests depends on the particular application. Under favorably controlled conditions, the method of the invention is capable of detecting positive test results much more rapidly than conventional culturing techniques. In medical testing, positive test results may be observed after less than eight hours, in some cases within 2 to 4 hours after inoculation. Therefore in medical laboratories, it may be desirable to test the character of the culture gas after intervals as short as one hour, repeating the test periodically either until positive results are observed or until it safely can be concluded that the sample is negative. The rapidity of the method of the invention is of particular advantage in the medical field where prompt results can be a matter of life or death.

In testing samples from batches of processed food products for bacterial contamination, repeated testing is neither necessary or desirable. In such situations it is preferred to make a single test of the character of the culture gas after a sufficiently long incubation period that there is a high probability that gas production has reached detectable levels in all positive samples. Incubation periods are limited by the capacity to store batches of processed products while awaiting the results of the tests of the samples and may range as long as 24 to 48 hours or longer.

After a short period of incubation, any bacteria or other biologically active agent present in the sample will begin to grow in the culture medium thereby consuming nutrients from the medium and producing metabolic byproducts. Fermentation of the $^{13}C$-labeled carbon source produces $^{13}CO_2$ which diffuses out of the culture medium into the culture gas. After a sufficient period of incubation for an appreciable amount of $^{13}CO_2$ to be formed, a sample of the culture gas is taken and the composition of the sample analyzed. After taking a culture gas sample, the vial and contents may be reincubated for additional periods, and the culture gas resampled and retested after each period, if desired.

FIG. 1 also schematically illustrates apparatus used for sampling the culture gas in a culture vial. The apparatus comprises a needle assembly generally designated by reference numeral 6 consisting of two hollow needles 7 and 8 respectively mounted in a stainless steel holder 9. Needle 7 is referred to as the outlet needle and is connected to a vacuum pump 10 by means of line 11, valve 12 and line 13. Valve 12 is also connected to line 14 which leads to a tapered fitting 15 adapted to engage a mating fitting 16 at the mouth of a removable sample bulb 17. A valve 18 is provided to close off the inlet of sample bulb 17.

The preferred procedure for sampling the culture gas begins by mating fittings 15 and 16 to secure sample bulb 17 to the needle assembly. Valve 12 is switched to connect lines 13 and 14; vacuum pump 10 is turned on, and valve 18 is opened so that sample bulb 17 is evacuated. When all the contents of bulb 17 have been removed by pump 10, valve 12 is switched to a closed position in which none of the lines, 11, 13, 14 are connected with each other. Needles 7 and 8 and septum 5 are sterilized, e.g., by wiping with 70% isopropanol and either burning off the alcohol in a flame or allowing it to evaporate, and the needle assembly 6 is forced against cap 4 until needles 7 and 8 penetrate septum 5. Sterilization of the septum and needles prevents contamination of culture medium 2 in vial 1. Once the needles have been inserted through the septum, valve 12 is switched to a position connecting lines 11 and 14 whereupon culture gas 3 from vial 1 passes into the evacuated sample bulb through needle 7, line 11, valve 12, line 14, joints 15 and 16 and valve 18. A submicron filter 19 interposed in line 11 prevents any of the culture medium which may have been sucked up along with the culture gas from passing into sample bulb 17. Line 11 also may be provided with a drying tube 20 filled with silica gel or other suitable drying agent to remove excess moisture from the culture gas sample. Replacement gas enters vial 1 through line 21 and inlet needle 8. A submicron filter 22 interposed in line 21 prevents dust, airborne bacteria and other contaminants from entering the culture vial with replacement gas.

It will be appreciated, particularly in the medical field, that prompt results and consequently short incubation times are highly desirable. At the same time, it will be appreciated that the shorter the incubation period, the less growth will take place in the culture and the less carbon dioxide will be produced. Consequently, it is desirable to be able to detect very small changes in carbon dioxide concentration of the culture gas. Since small changes may be more readily detected when there is a lower base level of carbon dioxide in the culture gas, it may be desirable to pass replacement culture gas, which enters the culture vial through line 21 and inlet needle 8, through a carbon dioxide trap to reduce the carbon dioxide content of the fresh culture gas to a consistent low level. The use of a carbon dioxide trap also tends to level out fluctuations in carbon dioxide content which may occur in the ambient atmosphere if ambient air is used as the culture gas. One possible arrangement is illustrated schematically in FIG. 1 wherein replacement culture gas (air) entering the culture vial through line 21 and needle 8 passes through a carbon dioxide trap 23. A molecular sieve, a soda lime preparation or a bubbling tube filled with an alkaline solution may be used as the carbon dioxide trap. A submicron filter 24 is shown interposed in line 21 between carbon dioxide trap 23 and needle 8 to prevent material from the trap from being drawn into vial 1 with the replacement air. However, it should be noted that low levels of $CO_2$ are not essential. Satisfactory detection of the presence or absence of biologically active agents can be carried out utilizing synthetic culture gases containing as much as 5% carbon dioxide.

Once sample bulb 17 is filled, valve 18 is closed and the sample bulb containing the culture gas sample can be removed for analysis. Use of a sample bulb having a substantially larger volume that the volume of the gas space in the culture vial enables substantially complete collection of the culture gas from the culture vial for subsequent analysis and, consequently, substantially complete replacement of the old culture gas from the culture vial with new culture gas. When repeated tests are carried out at periodic intervals on a single sample vial, it is possible in this way to provide a fresh culture gas atmosphere for each time segment. It should be noted, however, that complete replacement of the culture gas in the vial is not essential. It is to be considered within the scope of the invention to sample and test small portions of the culture gas within each vial.

Each culture gas sample is analyzed to determine the ratio of $^{13}CO_2$ to $^{12}CO_2$ in the sample. Since very small differences in gas content are being measured and since the temperature of the culture medium can affect the solubility of gases in the medium, maximum accuracy will be obtained only if care is taken to ensure that all vials in a given test are at the same temperature when culture gas samples are taken.

Analysis of the culture gas sample can be carried out in several different ways. One particularly preferred way of analyzing the culture gas sample is to take a mass spectrum of the gas sample and compare the relative peak heights of the M/e values corresponding to the molecular weights of $^{13}CO_2$ and $^{12}CO_2$. Naturally, analysis of the composition of the culture gas need not be limited to use of a mass spectrometer. Instead, any suitable means of analyzing the relative contents of $^{13}CO_2$ and $^{12}CO_2$ in the culture gas may be utilized. Additional methods of analysis which may be used include infrared absorption spectroscopy, laser heterodyne spectroscopy, laser induced fluorescence, modulated laser exicitation with opto-acoustic detection or nuclear magnetic resonance.

While analysis of the culture gas by means of a mass spectrometer requires withdrawal of at least a part of the culture gas from the culture vial, it is, of course, possible to analyze the culture gas without withdrawing any of the gas from the vial by inserting an appropriate analytical probe into the culture vial through a self-sealing rubber septum. For example, the relative concentrations of $^{13}CO_2$ and $^{12}CO_2$ could be determined with an infrared light pipe probe.

When no subsequent measurements of the $^{13}CO_2$ to $^{12}CO_2$ ratio of a particular via are contemplated, the culture medium may be acidified by injection of a small amount of acid such as hydrochloric or sulfuric to release carbon dioxide from solution in the medium into the culture gas atmosphere, thereby to provide a more sensitive test.

The method of the invention requires a comparison of the ratio of $^{13}CO_2$ to $^{12}CO_2$ in the culture gas from an incubated test vial to a reference standard representing the initial $^{13}CO_2/^{12}CO_2$ ratio of the culture gas in order to detect changes in composition of the culture gas due to the presence of one or more biologically active agents. The reference standard may be developed either by directly measuring the initial culture gas composition prior to incubation of the test vial or by simultaneously measuring the composition of the gas from an uninoculated control vial initially containing the same culture gas after subjection to a parallel incubation treatment. The latter procedure has the advantage of compensating for any gases produced by thermal degradation of the culture medium during the incubation period and of allowing all measurements to be made at one time. The former procedure has the advantage of requiring only a single culture vial. If cylinder gas is used as the culture gas, it may not be necessary to redetermine the initial $^{13}CO_2$ to $^{12}CO_2$ ratio of the culture gas with each test. Instead, a single analysis of the gas composition from a cylinder may be used as the reference standard for all tests run with gas from that cylinder.

An appreciable difference between the $^{13}CO_2$ to $^{12}CO_2$ ratio of the post-incubation culture gas sample and the initial culture gas ratio indicates the presence of some biologically active agent in the test material. By an appreciable difference is meant a difference greater than the ordinary maximum statistical deviation to be expected for the analytical technique used to measure the relative amounts of $^{13}CO_2$ and $^{12}CO_2$ in the culture gas or attributable to minor variations in experimental conditions, e.g., vial temperature, between identical samples.

When analysis of the composition of the culture gas samples is carried out by taking mass spectra of the gas samples and comparing the relative sizes of the M/e 45 and M/e 44 peaks to determine the ratio of singly labeled $^{13}CO_2$ to $^{12}CO_2$, the worst case probable error can be estimated statistically. Differences in ratios greater than twice the worst case probable error can be considered appreciable.

EXAMPLE I

Figure 2:
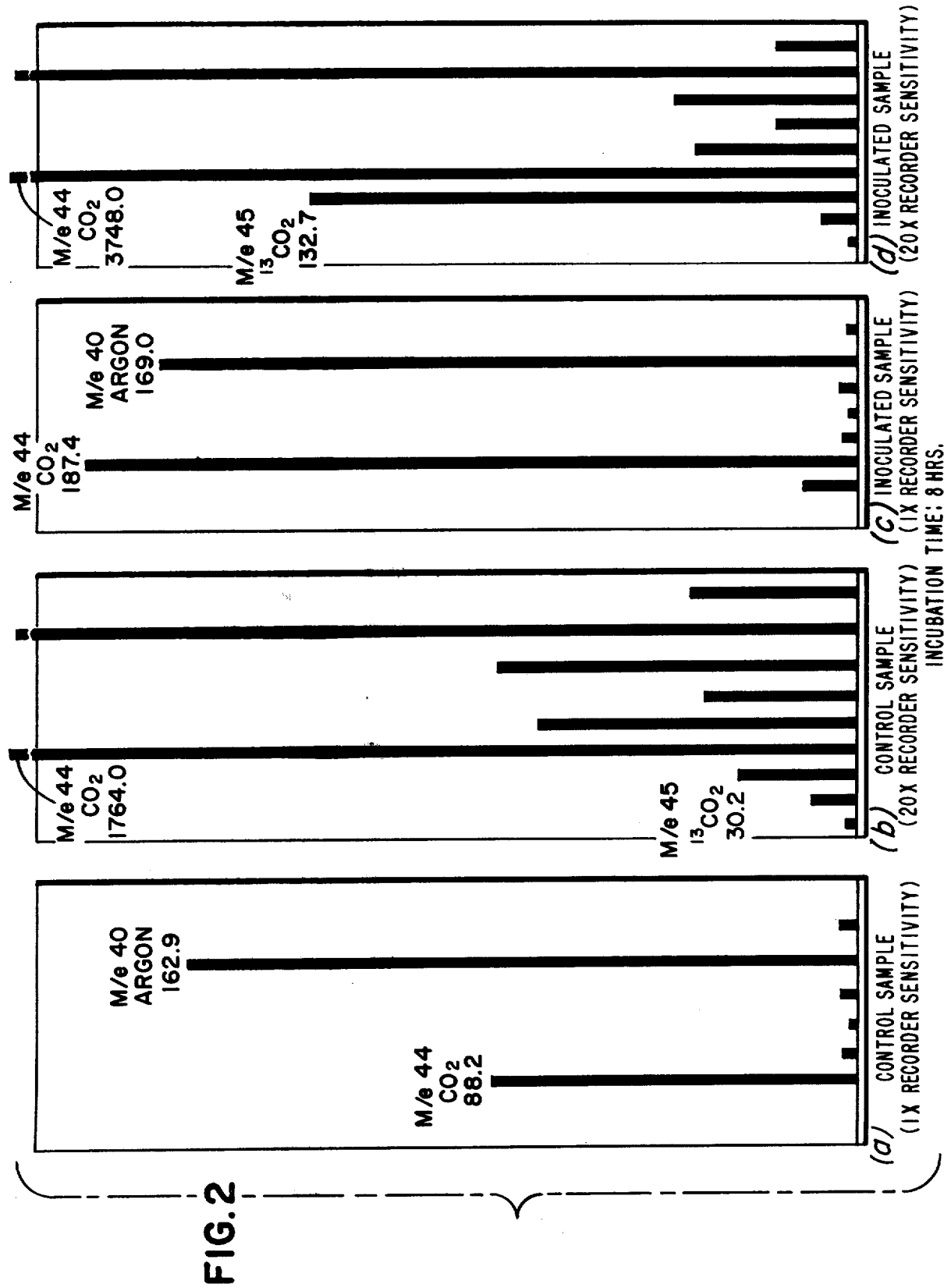
FIG. 2 depicts representative mass spectrometric data from an actual test of the invention.

FIG. 2 shows comparative mass spectra of samples of culture gas taken from an uninoculated control vial and a vial inoculated with an overnight culture of *Pseudomonas pseudoalkaligenes*. The size of each inoculum was 0.5 ml. Each culture vial was a standard 50 cc vial containing approximately 30 ml. tryptic soy broth culture medium fortified with $^{13}C$-labeled glycine. Both the control sample and the inoculated sample were incubated for a period of 8 hours at 37° C. with mild agitation before withdrawal of the culture gas samples whose spectra are shown in FIG. 2. Spectra were taken with a Perkin-Elmer Hitachi model RMU-6 mass spectrometer. Operating parameters of the spectrometer are given in Table I:

TABLE I

Mass Spectrometer Parameters

Electron Energy = 70eV
Ionization (Target) Current = 50 μ A
Mass Range = 450 a.m.u.
Accelerating Voltage = 2450V.
Head Amplifier Setting = X10
Ion Multiplier High Voltage = 1.5KV, 1.75KV
Ion Entrance Slit = 0.19 mm
Ion Exit Slit = 1.00 mm
Magnet Scan Rate = 6
Start Scan Set: Coarse = 140, 240
　　　　　　　　　Fine = 0, 0
Background Analyzer Pressure = $1.8 \times 10^{-7}$ mmHg
Analyzer Pressure with Sample = $7.5 \times 10^{-7}$ mmHg
Recorder Sensitivity: 1.0V, 0.5V, 0.2V, 0.1V
　　　　　　　　　　0.05V, 0.02V
Recorder X-Axis Drive = 20 mm/min
Gas Sample System Pressure = 6 mmHg
Sampling Sub-volume filled, emptied
4 times into reservoir FIGS. 2(a) and 2(b) are mass spectra of the culture gas from the uninoculated vial after 8 hours incubation. The spectrum of FIG. 2(b) was taken with the recorder set at 20 times the sensitivity used in taking the spectrum of FIG. 2(a) in order to provide increased amplification of the smaller spectrum peaks. FIGS. 2(c) and 2(d) are comparable mass spectra of the culture gas from the inoculated vial after 8 hours of incubation. Numerical values for the peak intensities for the spectra of FIG. 2 are given in Table 2.

TABLE II

| Vial | M/e 44 Peak Height mm | X20 | M/e 45 Peak Height mm | $^{13}CO_2$ $^{12}CO_2$ Ratios |
|---|---|---|---|---|
| Control | 88.2 | 1764.0 | 30.0 | .017 |
| Inoculated | 187.4 | 3748.0 | 132.7 | .036 |

The height of the M/e 44 (carbon dioxide) peak for the inoculated sample shown in FIG. 2(c) is 187.4 mm. while the height of the corresponding peak for the uninoculated control sample shown in FIG. 2(a) is 88.2 mm. Comparability of the two spectra is shown by the relatively constant peak height of the M/e 40 (argon) peaks which measure 160.9 mm. in FIG. 2(a) and 169.0 mm. in FIG. 2(c). In a similar vein, the M/e 45 ($^{13}CO_2$) peaks in the expanded scale spectra of FIG. 2(b) and FIG. 2(d) measure 30.0 mm. and 132.7 mm. respectively for the uninoculated control and the inoculated samples. For comparison purposes, the peak heights of the spectra in FIG. 2(a) and FIG. 2(c) are converted to a scale comparable to that of the peaks from FIGS. 2(b) and 2(d) by multiplying a factor of 20 and the ratio of the $^{13}CO_2$ peak to the $^{12}CO_2$ peak is computed for each sample to three significant figures. The $^{13}CO_2/^{12}CO_2$ peak height ratio for the uninoculated control sample is 0.017 while that for the inoculated sample is 0.036. The use of the $^{13}CO_2/^{12}CO_2$ ratio as a standard of comparison is necessary because of the presence of appreciable amounts of the $^{13}C$-isotope in all carbon. A mass spectrum of atmospheric air analyzed in the same manner as the culture gas samples from the inoculated and uninoculated vials yielded a $^{13}CO_2/^{12}CO_2$ ratio of 0.015. It is apparent that the ratio of $^{13}CO_2$ to $^{12}CO_2$ in the control via culture gas is substantially the same as in atmospheric air but that there has been an appreciable increase in the proportion of $^{13}CO_2$ in the inoculated vial. The greater proportion of $^{13}CO_2$ in the inoculated vial indicates metabolization of the $^{13}C$-labeled substrate has taken place in the inoculated vial, thereby establishing the presence of a biologically active agent in that vial.

contents. The culture gas atmospheres of vials 2, 3, and 4 were sampled after 4 hours incubation, and a mass spectrum was taken of each sample to measure the $^{13}CO_2$ and $^{12}CO_2$ contents. After 8 hours incubation, the culture gases of vials 2, 5, and 6, and after 12 hours incubation, the culture gases of vials 2, 7 and 8 were sampled and analyzed in like manner.

A 250 ml sample bulb was utilized. The larger volume of the sample bulb in comparison with the approximately 30 ml gas space of the culture vial ensures substantially complete withdrawal of the culture gas from the vial for measurement and, in retested vials, makes it possible to start each segment of the incubation period with fresh culture gas. Peak heights of each spectrum were proportionally adjusted to bring the argon peaks to a normalized peak height of 200 mm. The heights of the $^{13}CO_2$ and $^{12}CO_2$ peaks were then measured and the $^{13}CO_2$ to $^{12}CO_2$ ratios determined for each sample. In actual practice, to compensate for possible variations in the operation of the mass spectrometer, a series of scans was made of each sample and average peak heights were used in the calculations.

TABLE III

| Hours Incubated | Sample Number | $^{12}CO_2$ Peak Height mm | $^{13}CO_2$ Peak Height mm | $^{13}CO_2/^{12}CO_2$ Ratio ± .002 |
|---|---|---|---|---|
| | | Uninoculated Controls | | |
| 0 | #1 | 84 | 1.16 | .014 |
| 4 | #3 | 85 | 1.35 | .016 |
| 8 | #5 | 86 | 1.34 | .016 |
| 12 | #7 | 87 | 1.33 | .015 |
| | | Inoculated Test Samples | | |
| 0 | #2 | 53 | 0.90 | .017 |
| 4 | #4 | 120 | 2.91 | .024 |
| 8 | #6 | 192 | 15.3 | .080 |
| 12 | #8 | 154 | 11.4 | .075 |
| | | Retested Inoculated Sample | | |
| 0 | #2 | 53 | 0.90 | .017 |
| 4 | #2 | 119 | 2.87 | .024 |
| 8 | #2 | 226 | 19.3 | .086 |
| 12 | #2 | 263 | 33.9 | .129 |

EXAMPLE II

A tryptic soy broth culture medium was prepared by adding 27.5 grams of tryptic soy broth produced by Bioquest (BBL), Cockeysville, Maryland, to sufficient deionized water to product one liter of medium. Thirty ml. aliquots of medium were dispensed into eight 50 ml vials. The vials were each capped with self-sealing rubber septa, and 0.5 ml of a sterile 60 milligram per ml $^{13}C$-labeled glycine solution was injected into each vial. The culture media containing vials were then sterilized in an autoclave for 15 minutes at 15 psig. Four of the bottles were then each inoculated with 0.5 ml of an overnight culture of Pseudomonas pseudoalkaligenes. Inoculated vials were assigned even numbers, and control vials were assigned odd numbers. Immediately after inoculation the gas space of each vial was flushed with ambient air to provide a fresh culture gas atmosphere in each vial and ensure that all vials has a substantially identical culture gas atmosphere. Before entering the vial, the flushing gas was passed through a submicron filter to remove dust and airborne bacteria and through a carbon dioxide trap consisting of a bubble tower containing 2 molar sodium hydroxide to stabilize the carbon dioxide content. All eight test bottles were then incubated at 35° C. with gentle agitation provided by mechanical shaking. The culture gas of vials 1 and 2 was immediately sampled and later analyzed with a mass spectrometer to determine the initial $^{13}CO_2$ and $^{12}CO_2$ After 6 hours incubation, a sample of ambient air passed through the filter and carbon dioxide trap was collected and its mass spectrum taken to provide a base reference value for the initial ratio of $^{13}CO_2$ to $^{12}CO_2$ in the culture gas. The ratio of $^{13}CO_2$ to $^{12}CO_2$ in the ambient air spectrum was 0.014.

Figure 3:
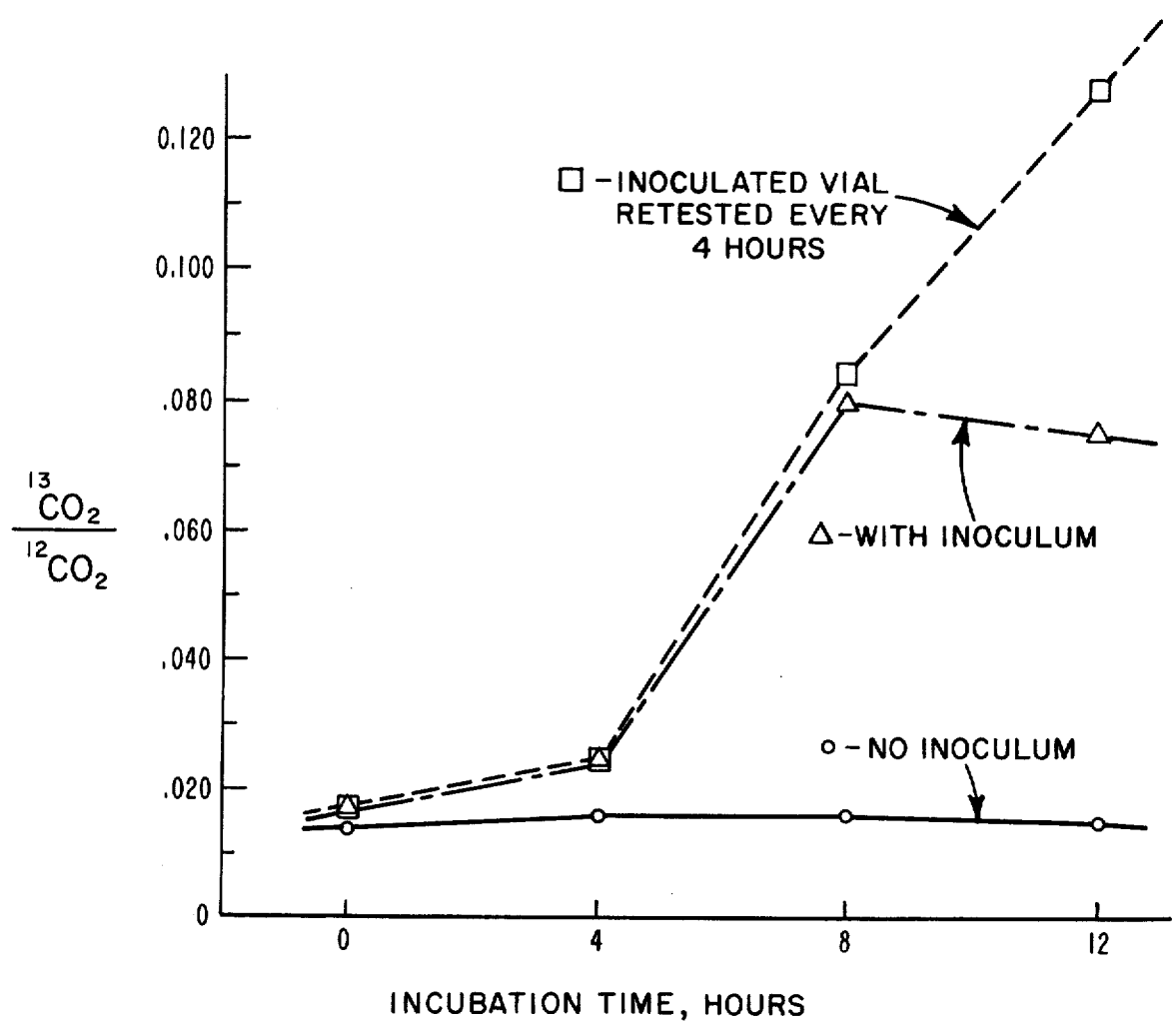
FIG. 3 is a graphic representation of the results from an experiment demonstrating the effectiveness of the method of the invention.

The ratios of $^{13}CO_2$ to $^{12}CO_2$ for each set of samples is plotted graphically in FIG. 3. Consideration of FIG. 3 reveals that there is no substantial change in the ratio of $^{13}CO_2$ to $^{12}CO_2$ in the culture gas in the uninoculated control vials, but that in the inoculated vials the ratio of $^{13}CO_2$ to $^{12}CO_2$ in the culture gas increases significantly thereby indicating metabolization of the $^{13}C$-labeled substrate and establishing the presence of a biologically active agent. Unambiguously positive results are observed in the first tests after only 4 hours incubation. Despite the low absolute values of the initial measurements of $^{13}CO_2$ and $^{12}CO_2$ in vial No. 2, the resulting ratio appears consistent and reliable. No cause is presently known for the apparently anomalous $^{13}CO_2$ to $^{12}CO_2$ ratio in vial No. 8.

EXAMPLE III

A sterile vial fitted with a dual closure system comprising a threaded cap and an opening closed with a rubber septum is partially filled with tryptic soy broth, and the vial and culture medium are sterilized. Sterile $^{13}$C-labeled glucose is injected into the vial. The threaded closure is opened, and a small amount of processed baby food is introduced into the vial after which the threaded closure is resealed. The gas space within the vial is flushed with a fresh culture gas, and a sample of the culture gas is taken for analysis of the $^{13}CO_2$ to $^{12}CO_2$ ratio. The vial and its contents are thereafter incubated for a period of 48 hours at 30° C. after which a second sample of the culture gas is taken for analysis of the relative proportions of $^{13}CO_2$ and $^{12}CO_2$. The post-incubation culture gas sample contains an appreciably greater proportion of $^{13}CO_2$ than the initial culture gas sample indicating metabolization of the $^{13}$C-labeled substrate and the presence of bacterial contamination of the baby food.

The foregoing embodiments have been described solely for purposes of exemplification and not by way of limitation. Since modifications of the disclosed embodiments may occur to persons skilled in the art, the scope of the invention is to be limited solely by the scope of the appended claims.

What is claimed is:

1. A method for detecting the presence of biologically active agents comprising the steps of:
   (a) providing a sterile, sealable container partially filled with a sterile, non-radioactive culture medium comprising a $^{13}$C-labeled substrate fermentable to produce singly labeled $^{13}C^{16}O_2$; the remainder of said container being filled with a culture gas; said container comprising means for introducing a sample of material to be tested for the presence of biologically active agents into the container;
   (b) introducing a sample of material to be tested for biological activity into said container and sealing said container;
   (c) subjecting the sealed container and its contents to conditions conductive to biological activity for a predetermined period of time up to 48 hours sufficient for fermentation of the $^{13}$C-labeled substrate to produce singly labeled $^{13}C^{16}O_2$;
   (d) thereafter measuring the relative proportions of $^{13}CO_2$ and $^{12}CO_2$ in the culture gas and determining the ratio of singly labeled $^{13}C^{16}O_2$ to $^{12}CO_2$ in the culture gas in the container, and
   (e) comparing the ratio determined in step (d) to a reference standard representing the initial ratio of singly labeled $^{13}C^{16}O_2$ to $^{12}CO_2$ in the culture gas to ascertain whether there has been an increase in the ratio of $^{13}C^{16}O_2$ to $^{12}CO_2$ indicative of the presence of a biologically active agent.

2. A method as recited in claim 1 wherein said sealed container is subjected to conditions conducive to biological activity for a period of between 1 and about 8 hours.

3. A method as recited in claim 2 wherein said sealed container is subjected to conditions conducive to biological activity for a period of between about 2 and about 4 hours.

4. A method as recited in claim 1 wherein the culture medium comprises tryptic soy broth.

5. A method as recited in claim 1 wherein the sealed container is subjected to conditions conducive to biological activity by maintaining the contents at a temperature lying in the range from about 35° C. to about 37° C. and agitating the culture medium.

6. A method as recited in claim 1 wherein the ratio of $^{13}C^{16}O_2$ to $^{12}CO_2$ in the culture gas is determined by taking a mass spectrum of the culture gas and comparing the amplitude of the M/e 45 peak to the amplitude of the M/e 44 peak.

7. A method as recited in claim 1 wherein the ratio of $^{13}C^{16}O_2$ to $^{12}CO_2$ in the culture gas is repeatedly measured at periodic intervals during the period of subjection to conditions conducive to biological activity and each measured ratio is compared to the initial ratio of $^{13}C^{16}O_2$ to $^{12}CO_2$ in the culture gas whereby to follow the biological activity of the test material with respect to time.

8. A method as recited in claim 1 wherein said sample of material to be tested is a fluid, said means to facilitate the introduction of said test material into the container comprises a self-sealing rubber septum, and the introduction of said test sample into container is effected by injecting said sample through said septum with a hypodermic syringe.

9. A method as recited in claim 1 wherein said $^{13}$C-labeled substrate is $^{13}$C- labeled glycine.

10. A method as recited in claim 1 wherein said $^{13}$C-labeled substrate is $^{13}$C- labeled glucose.

11. A method for detecting the presence of biologically active agents comprising the steps of:
    (a) providing a sterile, sealable container partially fillied with a previously sterilized culture medium to which has been added a sample of material to be tested for the presence of biological activity; said medium comprising a $^{13}$C-labeled substrate fermentable to produce singly labeled $^{13}C^{16}O_2$; the remainder of said container being filled with a culture gas containing a known initial ratio of singly labeled $^{13}C^{16}O_2$ to $^{12}CO_2$;
    (b) subjecting the sealed container and its contents to conditions conductive to biological activity for a predetermined period of time up to 48 hours sufficient for fermentation of the $^{13}$C-labeled substrate to produce singly labeled $^{13}C^{16}O_2$;
    (c) thereafter measuring the relative proportions of $^{13}CO_2$ and $^{12}CO_2$ in the culture gas and determining the ratio of singly labeled $^{13}C^{16}O_2$ to $^{12}CO_2$ in the culture gas in the container; and
    (d) comparing the ratio determined in (c) to the known initial ratio of singly labeled $^{13}C^{16}O_2$ to $^{12}CO_2$ in the culture gas to ascertain whether there has been an increase in the ratio of singly labeled $^{13}C^{16}O_2$ to $^{12}CO_2$ indicative of the presence of a biologically active agent.

12. A method for detecting the presence of biologically active agents comprising the steps of:
    (a) providing a sterile, sealable container partially filled with a sterile, non-radioactive culture medium comprising a $^{13}$C-labeled substrate fermentable to produce singly labeled $^{13}C^{16}O_2$, the remainder of said container being filled with a culture gas; said container comprising means for introducing a sample of material to be tested for the presence of biologically active agents into the container;
    (b) introducing a sample of material to be tested fo biological activity into said container and sealing said container;
    (c) determining the initial ratio of singly labeled $^{13}C^{16}O_2$ to $^{12}CO_2$ in said culture gas;
    (d) subjecting the sealed container and its contents to conditions conductive to biological activity for a predetermined period of time up to 48 hours sufficient for fermentation of the $^{13}$C-labeled substrate to produce singly labeled $^{13}C^{16}O_2$;

(e) thereafter measuring the relative proportions of $^{13}CO_2$ and $^{12}CO_2$ in the culture gas and determining the ratio of singly labeled $^{13}C^{16}O_2$ to $^{12}CO_2$ in the culture gas in the container; and (f) comparing the ratio determined in step (e) to the initial ratio determined in step (c) to ascertain whether there has been an increase in the ratio of singly labeled $^{13}C^{16}O_2$ to $^{12}CO_2$ indicative of the presence of a biologically active agent.

13. A method for detecting the presence of biologically active agents comprising the steps of:

(a) providing a sterile, sealable container partially filled with a sterile, non-radioactive culture medium comprising a $^{13}C$-labeled substrate fermentable to produce singly labeled $^{13}C^{16}O_2$, the remainder of said container being filled with a culture gas containing a known initial ratio of singly labeled $^{13}C^{16}O_2$ to $^{12}CO_2$; said container comprising means for introducing a sample of material to be tested for the presence of biologically active agents into the container;

(b) introducing a sample of material to be tested for biological activity into said container and sealing said container;

(c) subjecting the sealed container and its contents to conditions conducive to biological activity for a predetermined period of time up to 48 hours sufficient for fermentation of the $^{13}C$-labeled substrate to produce singly labeled $^{13}C^{16}O_2$;

(d) thereafter withdrawing a sample of the culture gas from said container measuring the relative proportions of $^{13}CO_2$ and $^{12}CO_2$ in said culture gas sample and determining the ratio of singly labeled $^{13}C^{16}O_2$ to $^{12}CO_2$ in said culture gas sample; and (e) comparing the ratio determined in step (d) to the initial ratio of singly labeled $^{13}CO_2$ to $^{12}CO_2$ in the culture gas to ascertain whether there has been an increase in the ratio of singly labeled $^{13}C^{16}O_2$ to $^{12}CO_2$ indicative of the presence of a biologically active agent.

14. A method for detecting the presence of biologically active agents comprising the steps of:

(a) providing a pair of identical, sterile, sealable containers partially filled with equal amounts of a sterile, non-radioactive culture medium comprising a $^{13}C$-labeled substrate fermentable to produce singly labeled $^{13}C^{16}O_2$, the remainder of said container being filled with a culture gas;

(b) inoculating one of the containers by introducing a material to be tested for the presence of biological activity into that container and sealing both containers;

(c) subjecting the sealed containers and their contents to conditions conducive to biological activity for a predetermined period of time up to 48 hours sufficient for fermentation of the $^{13}C$-labeled substrate to produce singly labeled $^{13}C^{16}O_2$;

(d) thereafter measuring the relative proportions of $^{13}C^{16}O_2$ and $^{12}CO_2$ in the culture gas and determining the ratio of singly labeled $^{13}C^{16}O_2$ to $^{12}CO_2$ in the culture gas in each of said containers; and (e) comparing the ratios of singly labeled $^{13}C^{16}O_2$ to $^{12}CO_2$ in the inoculated and uninoculated containers to ascertain whether there is a difference in the ratios indicative of the presence of a biologically active agent in the inoculated container.

* * * * *